(12) United States Patent
Archuleta et al.

(10) Patent No.: US 10,258,792 B2
(45) Date of Patent: Apr. 16, 2019

(54) ENDOCARDIAL LEAD CUTTING APPARATUS

(71) Applicant: The Spectranetics Corporation, Colorado Springs, CO (US)

(72) Inventors: Andrew Archuleta, Penrose, CO (US); David Atwell, Colorado Springs, CO (US); Kenneth D. Harlan, Peyton, CO (US); Thomas E. Plasket, Colorado Springs, CO (US); Kevin D. Taylor, Colorado Springs, CO (US)

(73) Assignee: The Spectranetics Corporation, Colorado Springs, CO (US)

( * ) Notice: Subject to any disclaimer, the term of this patent is extended or adjusted under 35 U.S.C. 154(b) by 81 days.

(21) Appl. No.: 15/218,444

(22) Filed: Jul. 25, 2016

(65) Prior Publication Data

US 2016/0339232 A1 Nov. 24, 2016

Related U.S. Application Data

(62) Division of application No. 14/857,621, filed on Sep. 17, 2015, which is a division of application No. 11/187,553, filed on Jul. 22, 2005, now abandoned.

(51) Int. Cl.
*A61N 1/05* (2006.01)
*A61B 17/32* (2006.01)

(52) U.S. Cl.
CPC ...... *A61N 1/056* (2013.01); *A61B 17/320016* (2013.01); *A61B 17/320068* (2013.01);
(Continued)

(58) Field of Classification Search
CPC .... A61B 17/320068; A61B 17/320016; A61B 2017/32004; A61N 2001/0578; A61N 1/056
See application file for complete search history.

(56) References Cited

U.S. PATENT DOCUMENTS

| 837,614 A | 12/1906 | Dierzen |
| 1,755,535 A | 4/1930 | Bratrud |

(Continued)

FOREIGN PATENT DOCUMENTS

| GB | 2042902 A | 10/1980 |
| WO | 2003022157 A2 | 3/2003 |
| WO | 2004073524 A1 | 9/2004 |

OTHER PUBLICATIONS

Extended European Search Report for European Patent Application No. 06788509.5, dated Mar. 20, 2013, 13 pages.
(Continued)

*Primary Examiner* — Phong Son H Dang

(57) ABSTRACT

In some embodiments, without limitation, the invention comprises an apparatus for cutting an endocardial lead within a patient. The apparatus comprises a generally flexible tubular member having a proximal end and distal end. At least one blade or cutting surface is affixed to the distal end of the tubular member. The apparatus optionally includes an adjustment mechanism adapted to adjust the blade or cutting surface between an extended position and a retracted position. The blade or cutting surface engages the endocardial lead to cut the lead. Various embodiments include a v-shaped groove defining the cutting surfaces. Other embodiments may comprise a rotatable blade of an inner shaft rotating within the tubular member and cutting the lead received within the v-shaped groove, and blades or cutting surfaces functioning like guillotines or scissors retracting into a distal end of the tubular member.

8 Claims, 6 Drawing Sheets

(52) U.S. Cl.
CPC ........... *A61B 2017/32004* (2013.01); *A61N 2001/0578* (2013.01)

(56) References Cited

U.S. PATENT DOCUMENTS

| | | | | |
|---|---|---|---|---|
| 3,939,561 | A | * | 2/1976 | Nichols .................. B23D 21/08 30/107 |
| 4,274,414 | A | * | 6/1981 | Johnson ........... A61B 17/32002 606/170 |
| 4,471,777 | A | * | 9/1984 | McCorkle, Jr. ...... A61B 17/221 294/100 |
| 4,559,041 | A | | 12/1985 | Razi |
| 4,598,710 | A | * | 7/1986 | Kleinberg ........ A61B 17/32002 30/290 |
| 4,603,694 | A | * | 8/1986 | Wheeler .......... A61B 17/32002 604/22 |
| 4,660,267 | A | * | 4/1987 | Wheeler .......... A61B 17/32002 29/437 |
| 4,850,354 | A | * | 7/1989 | McGurk-Burleson ...................... A61B 17/32002 606/170 |
| 4,923,441 | A | * | 5/1990 | Shuler .............. A61B 17/32002 604/22 |
| 4,979,951 | A | * | 12/1990 | Simpson .......... A61B 17/22031 600/565 |
| 5,007,917 | A | * | 4/1991 | Evans ............... A61B 17/32002 604/22 |
| 5,052,402 | A | | 10/1991 | Bencini et al. |
| 5,112,299 | A | * | 5/1992 | Pascaloff ......... A61B 17/32002 604/22 |
| 5,123,904 | A | * | 6/1992 | Shimomura ..... A61B 17/32002 604/22 |
| 5,171,314 | A | | 12/1992 | Dulebohn |
| 5,176,128 | A | * | 1/1993 | Andrese ............. A61B 17/0218 600/204 |
| 5,197,971 | A | * | 3/1993 | Bonutti .............. A61B 17/0218 604/105 |
| 5,241,968 | A | * | 9/1993 | Slater ..................... A61B 17/29 600/564 |
| 5,269,798 | A | * | 12/1993 | Winkler ............ A61B 17/32002 30/345 |
| 5,275,609 | A | * | 1/1994 | Pingleton ......... A61B 17/32002 600/566 |
| 5,282,826 | A | | 2/1994 | Quadri |
| 5,409,454 | A | * | 4/1995 | Fischell ......... A61B 17/320783 604/22 |
| 5,437,630 | A | * | 8/1995 | Daniel ............. A61B 17/32002 604/22 |
| 5,471,992 | A | | 12/1995 | Banik et al. |
| 5,474,532 | A | * | 12/1995 | Steppe ................. A61F 9/00763 604/22 |
| 5,501,669 | A | * | 3/1996 | Conway .................. A61L 29/06 600/31 |
| 5,514,115 | A | * | 5/1996 | Frantzen ........ A61B 17/320783 604/531 |
| 5,540,708 | A | * | 7/1996 | Lim ................. A61B 17/32002 30/240 |
| 5,542,432 | A | | 8/1996 | Slater et al. |
| 5,549,623 | A | * | 8/1996 | Sharpe ........... A61B 17/320016 600/564 |
| 5,569,277 | A | * | 10/1996 | Evans ............. A61B 17/320783 604/22 |
| 5,582,617 | A | | 12/1996 | Klieman et al. |
| 5,591,187 | A | | 1/1997 | Dekel |
| 5,665,062 | A | * | 9/1997 | Houser .............. A61B 18/1492 604/22 |
| 5,665,101 | A | * | 9/1997 | Becker ............. A61B 17/32002 606/167 |
| 5,676,012 | A | * | 10/1997 | Ceriale ........... A61B 17/32002 606/170 |
| 5,709,697 | A | | 1/1998 | Ratcliff et al. |
| 5,733,297 | A | * | 3/1998 | Wang .................. A61F 9/00763 606/167 |
| 5,741,287 | A | * | 4/1998 | Alden .............. A61B 17/32002 604/22 |
| 5,766,177 | A | | 6/1998 | Lucas-Dean et al. |
| 5,766,199 | A | * | 6/1998 | Heisler ............ A61B 17/32002 606/170 |
| 5,779,715 | A | | 7/1998 | Tu |
| 5,810,883 | A | | 9/1998 | Lang |
| 5,820,630 | A | | 10/1998 | Lind |
| 5,863,294 | A | * | 1/1999 | Alden .............. A61B 17/32002 606/167 |
| 5,868,768 | A | | 2/1999 | Wicherski et al. |
| 5,873,886 | A | | 2/1999 | Larsen et al. |
| 5,904,681 | A | * | 5/1999 | West, Jr. ............ A61B 18/1485 604/22 |
| 5,913,867 | A | | 6/1999 | Dion |
| 5,931,847 | A | * | 8/1999 | Bittner ............. A61B 17/07207 227/180.1 |
| 6,004,335 | A | | 12/1999 | Vaitekunas et al. |
| 6,007,554 | A | * | 12/1999 | Van Ess ......... A61B 17/320016 604/22 |
| 6,033,402 | A | | 3/2000 | Tu et al. |
| 6,049,984 | A | * | 4/2000 | McGehee ............... A24F 13/24 131/248 |
| 6,051,005 | A | * | 4/2000 | Brandsey ....... A61B 17/320016 606/148 |
| 6,053,923 | A | * | 4/2000 | Veca ............... A61B 17/32002 606/79 |
| 6,053,928 | A | * | 4/2000 | Van Wyk ........ A61B 17/32002 606/167 |
| 6,110,177 | A | | 8/2000 | Ebner et al. |
| 6,139,508 | A | | 10/2000 | Simpson et al. |
| 6,142,997 | A | | 11/2000 | Michelson |
| 6,217,598 | B1 | * | 4/2001 | Berman ........... A61B 17/32002 606/167 |
| 6,241,692 | B1 | | 6/2001 | Tu et al. |
| 6,267,732 | B1 | | 7/2001 | Heneveld et al. |
| 6,383,146 | B1 | | 5/2002 | Klint |
| 6,419,684 | B1 | * | 7/2002 | Heisler ............ A61B 17/32002 600/567 |
| 6,428,539 | B1 | | 8/2002 | Baxter et al. |
| 6,432,115 | B1 | | 8/2002 | Mollenauer et al. |
| 6,443,966 | B1 | | 9/2002 | Shiu |
| 6,447,525 | B2 | | 9/2002 | Follmer et al. |
| 6,561,988 | B1 | | 5/2003 | Turturro et al. |
| 6,605,077 | B2 | | 8/2003 | Whittier et al. |
| 6,726,690 | B2 | * | 4/2004 | Eckman ............. A61B 17/1671 606/170 |
| 6,773,445 | B2 | | 8/2004 | Finlay et al. |
| 6,783,524 | B2 | | 8/2004 | Anderson et al. |
| 6,926,676 | B2 | | 8/2005 | Turturro et al. |
| 7,033,357 | B2 | * | 4/2006 | Baxter ........... A61B 17/320016 606/41 |
| 7,186,252 | B2 | * | 3/2007 | Nobis ............. A61B 17/320016 600/566 |
| 7,331,972 | B1 | * | 2/2008 | Cox ............... A61B 17/320016 606/170 |
| 7,699,846 | B2 | * | 4/2010 | Ryan ................ A61B 17/32002 606/170 |
| D624,653 | S | * | 9/2010 | Boillat ........................ D24/133 |
| 7,993,359 | B1 | | 8/2011 | Atwell et al. |
| 8,097,012 | B2 | | 1/2012 | Kagarise |
| 8,585,724 | B2 | * | 11/2013 | Palmer .............. A61B 10/0275 606/170 |
| 9,820,885 | B2 | * | 11/2017 | Sorensen ......... A61B 18/1482 |
| 2002/0156492 | A1 | * | 10/2002 | Timm ............. A61B 17/320068 606/169 |
| 2002/0177843 | A1 | | 11/2002 | Anderson et al. |
| 2003/0055417 | A1 | * | 3/2003 | Truckai .......... A61B 17/320092 606/27 |
| 2003/0078609 | A1 | | 4/2003 | Finlay et al. |
| 2004/0153096 | A1 | | 8/2004 | Goode et al. |
| 2005/0187571 | A1 | * | 8/2005 | Maschke ............. A61B 5/0066 606/159 |
| 2006/0095025 | A1 | * | 5/2006 | Levine ............ A61B 17/00234 606/15 |
| 2006/0241665 | A1 | | 10/2006 | Bosley et al. |

(56) References Cited

U.S. PATENT DOCUMENTS

| | | | | |
|---|---|---|---|---|
| 2006/0289602 | A1* | 12/2006 | Wales | A61B 1/005 227/180.1 |
| 2006/0293700 | A1* | 12/2006 | Dana | A61B 17/0467 606/148 |
| 2012/0095479 | A1 | 4/2012 | Bowe et al. | |
| 2016/0001064 | A1* | 1/2016 | Archuleta | A61N 1/056 606/15 |

OTHER PUBLICATIONS

International Preliminary Report on Patentability issued in PCT Application No. PCT/US2014/019258, dated Sep. 24, 2015, 12 pages.

International Preliminary Report on Patentability issued in PCT/US2006/028960, dated Jan. 29, 2008, 6 pages.

International Search Report and Written Opinion issued in PCT/US2006/028960, dated Apr. 9, 2007, 6 pages.

Notice of Allowance for U.S. Appl. No. 11/190,550 dated Sep. 15, 2011, 8 pages.

Notice of Allowance for U.S. Pat. No. 484,825 dated Feb. 11, 2011, 6 pages.

Official Action for U.S. Appl. No. 11/190,550 dated Apr. 4 2007, 8 pages.

Official Action for U.S. Appl. No. 11/190,550 dated Aug. 5, 2008, 9 pages.

Official Action for U.S. Appl. No. 11/190,550 dated Dec. 13, 2007, 9 pages.

Official Action for U.S. Appl. No. 11/190,550 dated Jan. 21, 2009, 8 pages.

Official Action for U.S. Appl. No. 11/190,550 dated Jan. 22, 2007, 5 pages.

Official Action for U.S. Appl. No. 11/190,550 dated Jan. 4, 2010, 7 pages.

Official Action for U.S. Appl. No. 11/190,550 dated Jun. 16, 2010, 8 pages.

Official Action for U.S. Pat. No. 484,825 dated Aug. 14, 2009, 6 pages.

Official Action for U.S. Pat. No. 484,825 dated Mar. 5, 2010, , 7 pages.

U.S. Appl. No. 11/187,553 entitled Endocardial Lead Cutting Apparatus, filed Jul. 22, 2005.

* cited by examiner

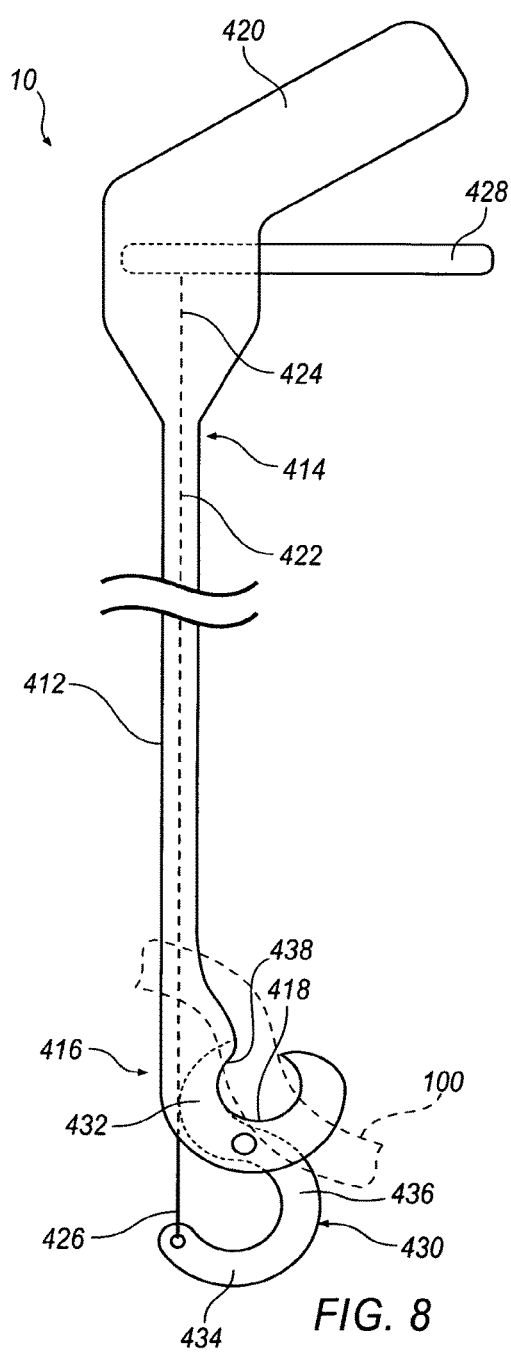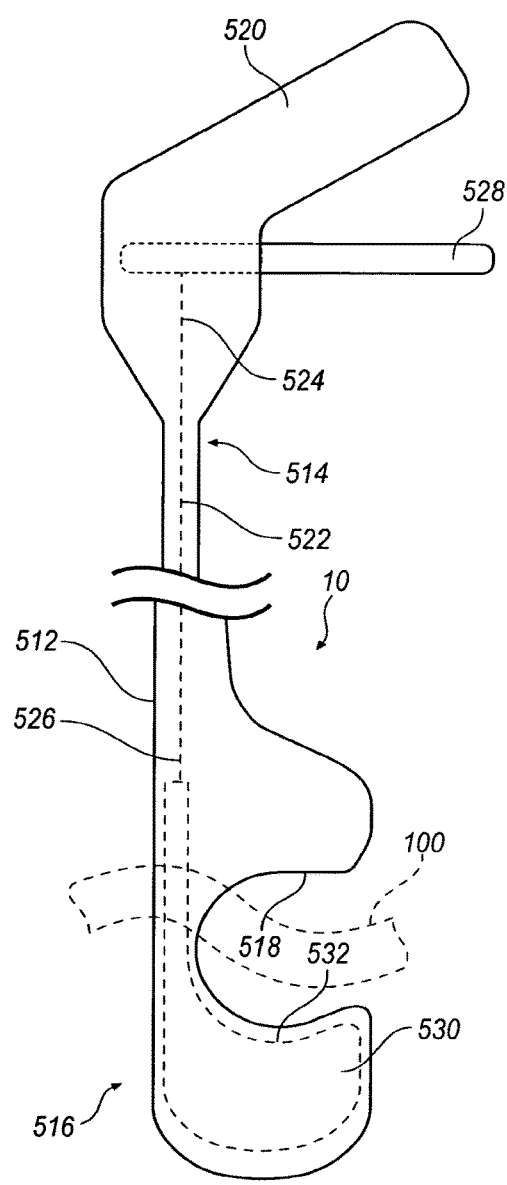

ENDOCARDIAL LEAD CUTTING APPARATUS

CROSS REFERENCE TO RELATED APPLICATION

The present application is a divisional of prior U.S. application Ser. No. 14/857,621, filed Sep. 17, 2015, entitled ENDOCARDIAL LEAD CUTTING APPARATUS, which is a divisional of U.S. application Ser. No. 11/187,553, filed Jul. 22, 2005, entitled ENDOCARDIAL LEAD CUTTING APPARATUS. Each of the above applications is specifically incorporated herein by reference in its entirety for all that it teaches and for all purposes.

FIELD OF THE INVENTION

This invention relates generally to an endocardial lead cutting apparatus and, more particularly, to an apparatus including at least one blade or cutting surface for cutting endocardial leads within a patient.

BACKGROUND OF THE INVENTION

In the past, various types of endocardial leads and electrodes have been introduced into different chambers of a patient's heart, including the right ventrical, right atrial appendage, and atrium as well as the coronary sinus. These flexible leads usually are composed of an insulator sleeve that contains an implanted helical coil conductor that is attached to an electrode tip. This electrode is placed in contact with myocardial tissue by passage through a venous access, often the subclavian vein or one of its tributaries, which leads to the endocardial surface of the heart chambers. The tip with the electrode contact is held in place by trabeculations of myocardial tissue.

The tips of many available leads include flexible tines, wedges, or finger-like projections which extend radially outward and usually are molded from and integral with the insulating sheath of the lead. These tines or protrusions allow surrounding growth of tissue in chronically implanted leads to fix the electrode tip in position in the heart and prevent dislodgement of the tip during the life of the lead. In "acute placement" of the electrode or lead tip, a blood clot forms about the flanges or tines (due to enzymes released as a result of irritation of the trabeculations of myocardial tissue by the presence of the electrode tip) until scar tissue eventually forms, usually in three to six months. The tines or wedges or finger-like projections allow better containment by the myocardial trabeculations of muscle tissue and prevent early dislodgement of the lead tip.

Although the state of the art in implemented pulse generator or pacemaker technology and endocardial lead technology has advanced considerably, endocardial leads nevertheless occasionally fail, due to a variety of reasons, including breakage of a lead, insulation breaks, breakage of the inner helical coil conductor and an increase in electrode resistance. Furthermore, in some instances, it may be desirable to electronically stimulate different portions of the heart than are presently being stimulated with the leads already implanted. There are a considerable number of patients who have one or more, and sometimes as many as four or five unused leads in their veins and heart.

Although it obviously would be desirable to easily remove such unused leads, in the past surgeons usually have avoided attempts to remove inoperative leads because the risk of removing them exceeded the risk of leaving them in.

The risks of leaving unused myocardial leads in the heart and venous path include increased likelihood that an old lead may facilitate infection, which in turn may necessitate removal of the lead to prevent continued bacteremia and abcess formation. Furthermore, there is an increased likelihood of the formation of blood clots in the atrial chamber about entangled leads. Such clots may embolize to the lung and produce severe complications and even fatality. Furthermore, the presence of unused leads in the venous pathway and inside the heart can cause considerable difficulty in the positioning and attachment of new endocardial leads in the heart.

Removal of an inoperative lead sometimes can be accomplished by applying traction and rotation to the outer free end of the lead, for example, if done prior to fixation of the lead tip in the trabeculations of myocardial tissue by scar tissue formation or large clot development. Even then, it is possible that a clot has formed so the removal of the leads causes various sized emboli to pass to the lungs, producing severe complications.

In cases where the lead tip has become attached by scar tissue to the myocardial wall, removal of the lead always has presented major problems and risks. Porous lead tips that are sometimes used may have an ingrowth of scar tissue attaching them to the myocardial wall. Sufficient traction on such leads in a removal attempt could cause disruption of the myocardial wall prior to release of the embedded lead tip. The tines or flanges of other types of leads that are not tightly scarred to the myocardial wall present similar risks. Even if screw-in tip electrodes are used, wherein the tips theoretically can be unscrewed from the myocardial wall, unscrewing of such tips may be prevented by a channel of scar tissue and endothelium that surrounds the outer surface of the lead along the venous pathway. Such "channel scar" tissue prevents withdrawal because of tight encasement of the lead. Continual strong pulling or twisting of the outer free end of the lead could cause rupture of the atrial wall or the ventricular wall if there is such tight circumferential encasement of adherent channel scar tissue in the venous path. Such tight encasement by scar tissue in the venous pathway and in the trabeculations of the myocardial wall typically occurs within six months to a year of the initial placement of the lead.

The risks of removing the lead by such traction and rotation of the lead are so high that, if it becomes imperative that the lead be removed (as in the case of infection), most surgeons have elected to open the patient's chest and surgically remove the lead rather than attempt removal by applying traction and rotation thereto.

Clearly, there is a need for an apparatus for extracting endocardial leads from a patient's heart with minimal risk to the patient.

SUMMARY OF THE INVENTION

To address these and other drawbacks, in some embodiments, without limitation, the present invention comprises an apparatus for cutting the lead as near as possible to an endocardial lead's embedded electrode.

Specifically, the present invention comprises an apparatus having a generally flexible tubular member having a proximal end and distal end. At least one blade or cutting surface is affixed to the distal end of the tubular member. In some embodiments, the apparatus includes an adjustment mechanism adapted to adjust the blade or cutting surface between an extended position and a retracted position.

Other aspects of the invention will be apparent to those skilled in the art after reviewing the drawings and the detailed description below.

BRIEF DESCRIPTION OF THE DRAWINGS

The present invention will now be described, by way of example, with reference to the accompanying drawings, in which:

FIG. 8 illustrates a perspective view of an endocardial lead cutting apparatus of a fourth embodiment of the present invention;

FIG. 9 illustrates a perspective view of an endocardial lead cutting apparatus of a fifth embodiment of the present invention;

DETAILED DESCRIPTION

Referring generally to FIGS. 1-11 and without limiting the scope of the embodiments of the invention, various embodiments of an apparatus are generally referred to at 10 for cutting an endocardial lead 100.

Figure 1:
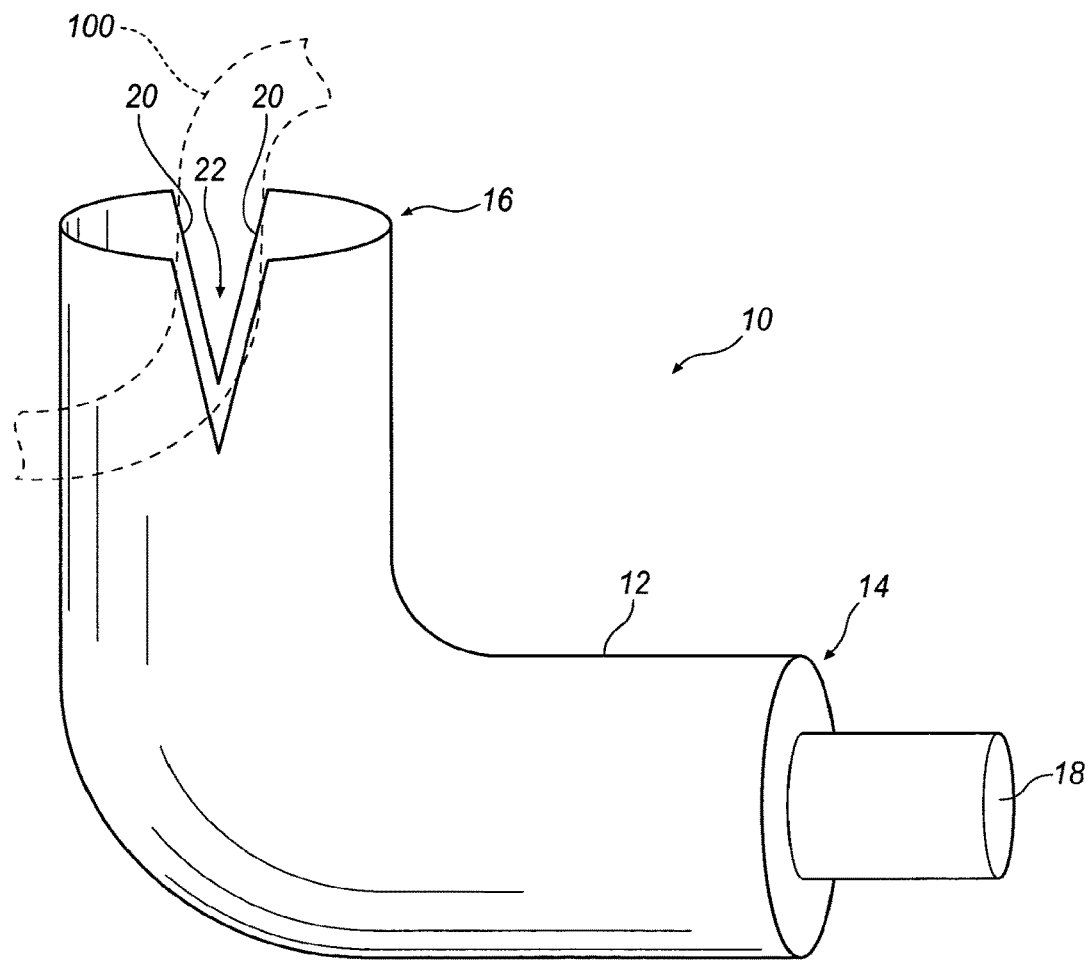
FIG. 1 illustrates a perspective view of an endocardial lead cutting apparatus of a first embodiment of the present invention.
Figure 2:
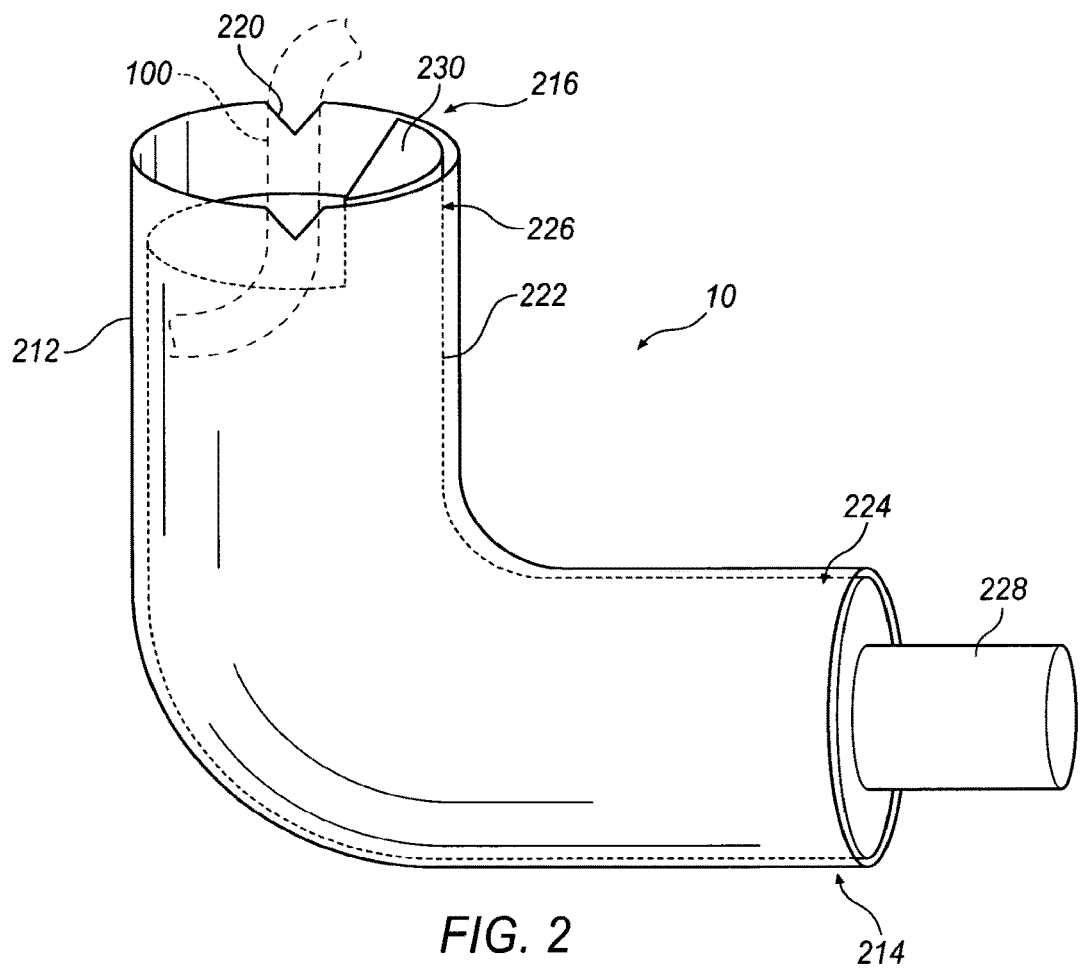
FIG. 2 illustrates a perspective view of an endocardial lead cutting apparatus of a second embodiment of the present invention.
Figure 3:
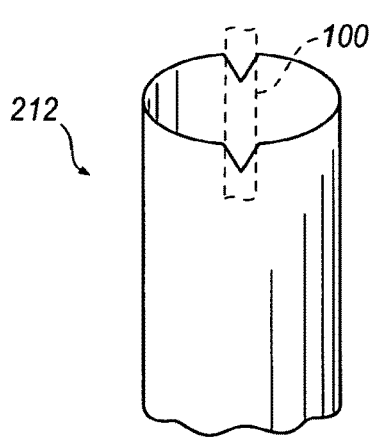
FIG. 3 illustrates an enlarged perspective view of a distal end of an outer tubular member of the second embodiment of the present invention.
Figure 4:
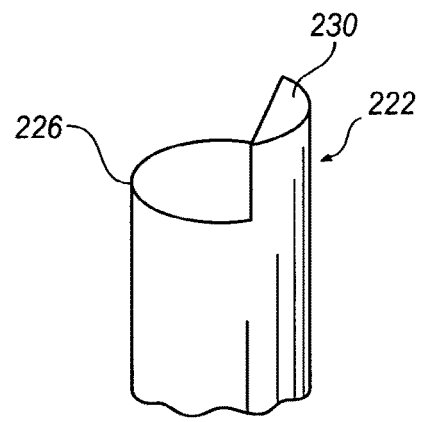
FIG. 4 illustrates an enlarged perspective view of a distal end of an inner shaft of the second embodiment of the present invention.
Figure 5A:
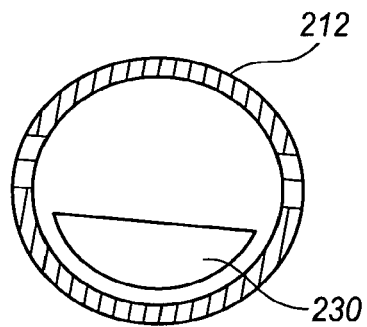
FIG. 5A-5C illustrate end views of the endocardial lead cutting apparatus of the second embodiment of the present invention having the inner shaft rotating to cut the lead.
Figure 5B:
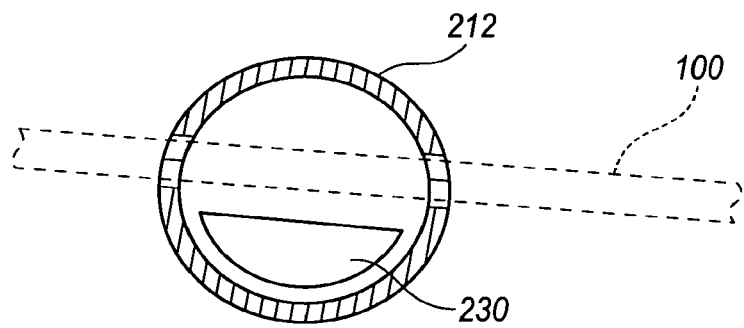
Figure 5C:
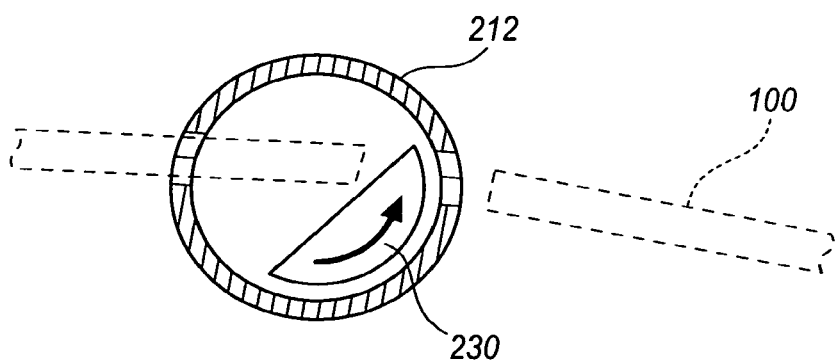

Referring to FIG. 1, the apparatus 10 of a first embodiment includes a shaft 12 having a proximal end 14 and a distal tip 16. The shaft 12 is generally flexible to facilitate movement of the apparatus 10 within the patient. The proximal end 14 of the shaft 12 includes a handle 18 while the distal tip 16 includes at least one cutting surface 20.

The at least one cutting surface 20 is defined by a groove 22 at the distal tip 16. The groove 22 is illustrated as generally v-shaped. Accordingly, as illustrated, the v-shaped groove 22 defines two cutting surfaces 20. Further, the cutting surfaces 20 are comprised of a generally hardened material, such as carbide and the like. While illustrated as a v-shaped groove 22, other configurations, such as u-shaped, c-shaped and the like are contemplated by the present invention.

Optionally, a shroud (not shown) is positioned about the shaft 12 such that a distal end of the shroud extends outwardly of the distal tip 16 of the shaft 12. The shroud is made of a generally pliable material to prevent damage to tissue of the patient prior to use of the apparatus 10.

Further, as an additional optional feature, the apparatus 10 may include a device (not shown) to provide an additional form of energy to cut the endocardial lead. By way of example, the device may be a laser generating device, an ultrasonic device, a vibration device and the like. The exemplary devices would apply radiation, ultrasonic waves or vibrations, respectively, to the lead 100 to assist in cutting the lead 100. In the example of a laser generating device, an optical fiber (not shown) would be disposed within the shaft 12 to transmit radiation from the proximal end 14 to the distal tip 16.

In operation, the first embodiment of apparatus 10 of FIG. 1 is inserted within a patient's heart (not shown) and the lead 100 (shown in phantom) is received within the groove 22 at the distal tip 16. When positioned to receive the lead 100 the pliable shroud is urged away from the distal tip 16 to expose the groove 22 and cutting surfaces 20. Linear and rotation motion is applied by way of the handle 18 to the shaft 12. The cutting surfaces 20 of the groove 22 then engages the lead. As additional pressure is applied the cutting surfaces 20 cut the lead and the apparatus 10 is removed from the patient. Optionally, when the lead 100 is received in the groove 22 the additional forms of energy such as radiation, ultrasound or vibration is applied to the lead to assist in cutting the lead 100.

A second embodiment of the apparatus 10 is shown in FIGS. 2-5. The second embodiment includes an outer tubular member 212 having a proximal end 214 and a distal end 216. The outer tubular member 212 is generally flexible to facilitate movement of the apparatus 10 within the patient. The distal end 216 includes a groove 220 for receiving the lead 100. As illustrated, the groove 220 is generally v-shaped for receiving the lead 100; however, other configurations are also contemplated by the present invention.

An inner shaft 222 is received within the outer tubular member 212. The inner shaft 222 includes a proximal end 224 and a distal end 226. Further, the inner shaft 222 is generally flexible and includes a handle 228 disposed at the proximal end 224. Positioned at the distal end 226 of the inner shaft is a blade 230. The blade 230 and the inner shaft 222 is made from a generally hardened material, such as carbide and the like, and rotates within the outer tubular member 212 to cut the lead 100 received within the groove 220 of the outer tubular member 212. The inner shaft 222 and blade 230 are rotatable in either direction.

Further, as described with respect to the first embodiment of FIG. 1, the apparatus 10 may include a shroud (not shown). The shroud is positioned about the outer tubular member 212 such that a distal end of the shroud extends outwardly of the distal end 216 of the outer tubular member 212. The shroud is made of a generally pliable material to prevent damage to tissue of the patient prior to use of the apparatus 10.

In operation, the second embodiment of apparatus 10 of FIGS. 2-5 is inserted within a patient's heart and the lead 100 is received within the groove 220 at the distal end 216 of the outer tubular member 212. When receiving the lead 100 within the groove 220, the inner shaft 222 and blade 230 are in a home position such that the blade 230 is generally offset from the groove 220. A positioning mechanism (not shown) may be included to bias the inner shaft 222 and blade 230 to the home position within the outer tubular member 212. When positioned to receive the lead 100 the pliable shroud is urged away from the distal end 216 to expose the groove 220 and blade 230. When the distal end 216 of the outer tubular member 212 is positioned as close as possible to the embedded electrode of the lead, the handle 228 of the inner shaft 222 is rotated and the blade 230 contacts the lead. Further rotation of the inner shaft 222 and the blade 230 cuts the lead 100. The apparatus 10 is then removed from the patient.

Figure 6:
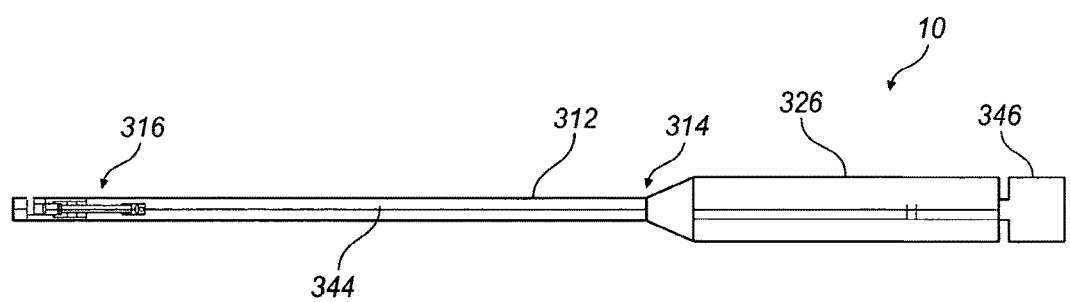
FIG. 6 illustrates a cross-sectional view of an endocardial lead cutting apparatus of a third embodiment of the present invention.
Figure 7:
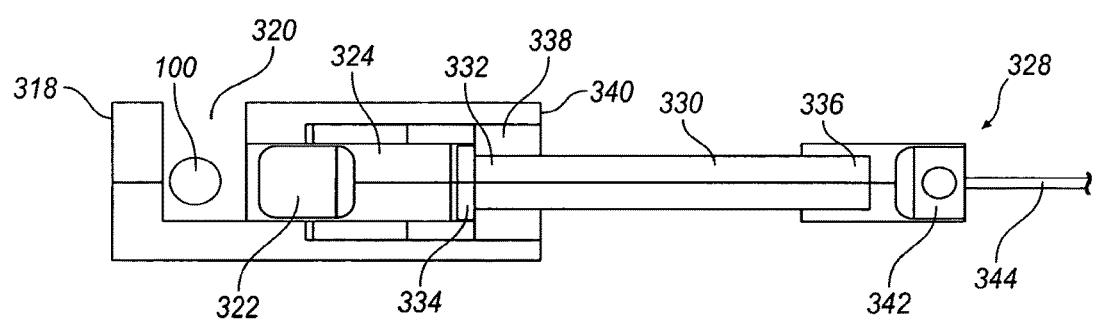
FIG. 7 illustrates an enlarged cross-sectional view of a distal end of the endocardial lead cutting apparatus of the third embodiment of the present invention.

Now referring to FIGS. 6-7, a third embodiment of the apparatus 10 of the present invention is illustrated. The apparatus 10 includes a tubular member 312 having a proximal end 314 and a distal end 316. The tubular member 312 is generally flexible and preferably made from a plastic or elastomeric material.

A housing 318 is generally disposed at the distal end 316 of the tubular member 312. The housing 318 includes an opening 320 for receiving the endocardial lead 100. Preferably, the housing 318 is made of stainless steel and is joined to the distal end 316 of the tubular member 312 by use of an adhesive. However, any technique for joining the housing 318 and the distal end 316 of the tubular member 312 is contemplated by the present invention.

Disposed within the housing 318 are a blade 322 and a plunger 324. The blade 322 is received within the plunger 324, preferably by press-fitting the blade 322 within the plunger 324. The blade 322 is made of carbide and moveable between an extended position and a retracted position. When in the extended position, the blade 322 is received within the opening 320 of the housing 318 to cut the lead 100 received therein.

The tubular member 312 includes a handle 326. The handle 326 is joined to the proximal end 314 of the tubular member 312 by adhesive and the like. Alternately, the handle 326 is press fit within the proximal end 314 of the tubular member 312. The handle 326 is utilized to actuate the blade 322 between the extended and retracted positions.

Further, the apparatus 10 of the third embodiment includes an adjustment mechanism generally referred to at 328. The adjustment mechanism 328 moves the blade 322 between the extended and retracted positions. Specifically, the adjustment mechanism 328 may comprise a screw 330. A first end 332 of the screw 330 is received at a proximal end 334 of the plunger 324. A second end 336 of the screw 330 extends through a retainer 338. The retainer 338 is generally disposed at a proximal end 340 of the housing 318.

The adjustment mechanism 328 further includes a universal joint 342 and drive wire 344. The universal joint 342 is disposed at the second end 336 of the screw 330. The universal joint 342 is also attached to the drive wire 344. The drive wire 344 extends through the tubular member 312 and attaches to the handle 326. Further, the handle 326 includes a knob 346. The knob 346 rotates to adjust the blade 322 between the extended and retracted positions.

In operation, the apparatus 10 of the third embodiment of the present invention of FIGS. 6-7 is inserted within a patient's heart and receives the lead 100 within the opening 320 of the housing 318. The adjustment mechanism 328 is actuated by rotating the knob 346. Rotational motion from the knob 346 is transferred through the drive wire 344 and universal joint 342 to rotate the screw 330. Rotation of the screw 330 advances the screw through the retainer 338 to move the plunger 324 and blade 322 from the retracted position to the extended position. Accordingly, the blade 322 is received in the opening 320 of the housing 318 and contacts the endocardial lead 100. The lead 100 is then cut by further extension of the blade 322 and the apparatus 10 is removed from within the patient.

Referring to FIG. 8, the fourth embodiment of the apparatus 10 of the present invention is illustrated. The apparatus 10 includes a tubular member 412 having a proximal end 414 and a distal end 416. The distal end 416 is generally u-shaped to define a first cutting surface 418. At the proximal end 414 of the tubular member 412 is a handle 420. The tubular member 412 may be generally flexible to move within the patient.

Disposed within the tubular member 412 is a tension member 422. The tension member 422 includes a proximal end 424 and a distal end 426. The proximal end 424 of the tension member 422 is fixed to a lever 428. The distal end 426 of the tension member 422 is fixed to a blade 430. The blade 430 is pivotally connected to the distal end 416 of the tubular member 412 and actuation of the lever 428 about the handle 420 pivots the blade 430 to capture the lead 100 between the blade and the first cutting surface 418.

Further, blade 430 has a generally s-shaped configuration and defines a first end 432, a second end 434 and a connecting leg 436 extending therebetween. The first end 432 includes an inner surface that defines a second cutting surface 438. The second end 434 is fixed to the proximal end 424 of the tension member 422. The connecting leg 436 of the blade 430 is pivotally connected to the distal end 416 of the tubular member 412. As illustrated the blade 430 is connected to the distal end 416 of the tubular member 412 generally at the midpoint of the connecting leg 436. However, alternative fastening positions or techniques are easily contemplated by one skilled in the art.

In operation, the apparatus 10 of the fourth embodiment is placed within a patient and the lead 100 is received within the u-shaped distal end 416 of the tubular member 412 such that the first cutting surface 418 contacts the lead 100. The lever 428 is actuated about the handle 420 to draw the tension member 422 away from the distal end 416 and pivot the blade 430 thereabout. When the blade 430 is pivoted, the second cutting surface 438 of the first end 432 also contacts the lead 100 to capture the lead 100 therebetween. Further actuation of the lever 428 and the cutting surfaces 418, 438 cut through the endocardial lead 100.

Referring to a fifth embodiment of FIG. 9, the apparatus 10 includes a tubular member 512 having a proximal end 514 and a distal end 516. The distal end 516 is generally c-shaped to define a first cutting surface 518. At the proximal end 514 of the tubular member 512 is a handle 520. The tubular member 512 may be generally flexible to move within the patient.

Disposed within the tubular member 512 is a tension member 522. The tension member 522 includes a proximal end 524 and a distal end 526. The proximal end 524 of the tension member 522 is fixed to a lever 528. The distal end 526 of the tension member 522 is fixed to a blade 530. The blade 530 is received within the tubular member 512 and disposed at the distal end 516. Actuation of the lever 528 about the handle 520 linearly moves the blade 530 to capture the lead 100 between the blade 530 and the first cutting surface 518. The blade 530 defines a second cutting surface 532 and capturing the lead 100 between the blade 530 and the first cutting surface 518 cuts the lead 100.

In operation, the apparatus 10 of the fifth embodiment is placed within a patient and the lead 100 is received within the c-shaped distal end 516 of the tubular member 512 such that the first cutting surface 518 contacts the lead 100. The lever 528 is actuated about the handle 520 to draw the tension member 522 away from the distal end 516 and move the blade 530 linearly. When the blade 530 is moved, the second cutting surface 532 of the blade 530 also contacts the lead 100 to capture the lead 100 between the blade 530 and the first cutting surface 518. Further actuation of the lever 528 and the cutting surfaces 518, 532 cut through the endocardial lead 100.

Figure 10:
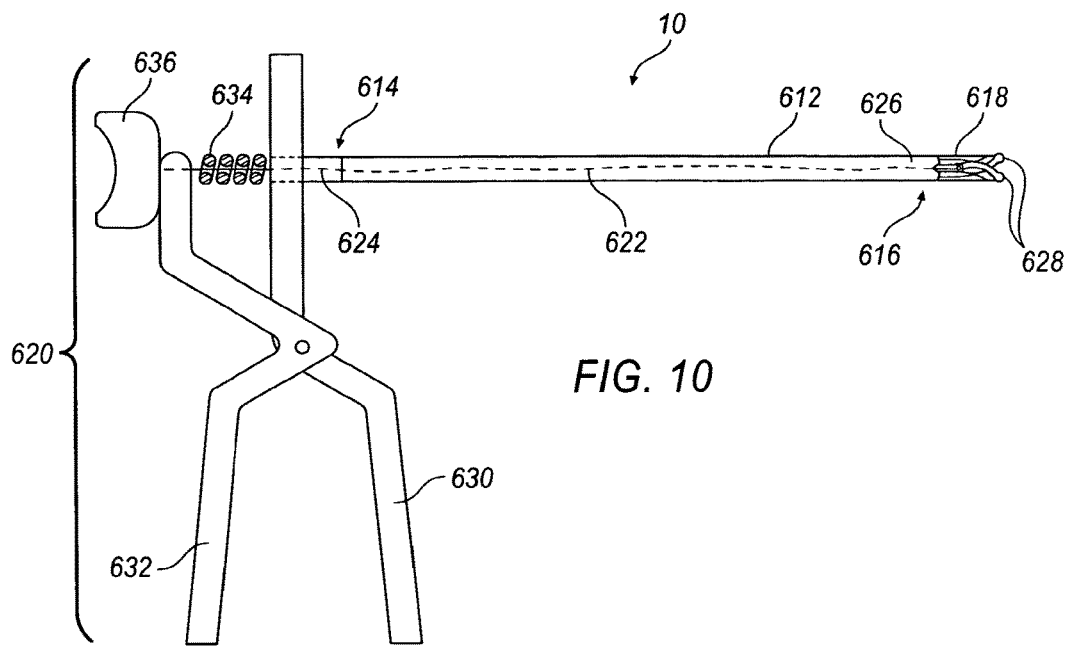
FIG. 10 illustrates a perspective view of an endocardial lead cutting apparatus of a sixth embodiment of the present invention.

Now referring to FIGS. 10-11, the sixth embodiment of apparatus 10 of the present invention is illustrated. The apparatus 10 includes a tubular member 612 having a proximal end 614 and a distal end 616. The distal end 616 includes a housing 618 while the proximal end 614 includes an adjustment mechanism 620. The tubular member 612 may be generally flexible to move within the patient and optionally include reinforcements such as a braid or compressed coil to strengthen the tubular member 612 and resist compression during operation.

Disposed within the tubular member 612 is a tension member 622. The tension member 622 includes a proximal end 624 and a distal end 626. The proximal end 624 of the tension member 622 is fixed to the adjustment mechanism 620 while the distal end 626 is connected to two blades 628. The adjustment mechanism 620 moves the tension member 622 and the blades 628 between an extended position and a retracted position.

The adjustment mechanism 620 includes a handle 630 for actuating the tension member 622 and blades 628 between the extended and retracted positions. Pivotally connected to the handle 630 is a lever 632 with a biasing mechanism 634, such as a spring and the like, disposed therebetween. The biasing mechanism 634 urges the lever 632 about the handle 630 and hence, the tension member 622 and blades 628 to one of either the extended or retracted positions. Optionally, the adjustment mechanism 620 may also include a knob 636 for actuating the tension member 622 and blades 628 to a position opposite of the bias of the handle 630 and lever 632 configuration. Further, various alternatives for actuating the tension member 622 and blades 628 between positions are contemplated by the present invention, especially techniques previously described in the present application.

Figures 11A, 11B, 11C:
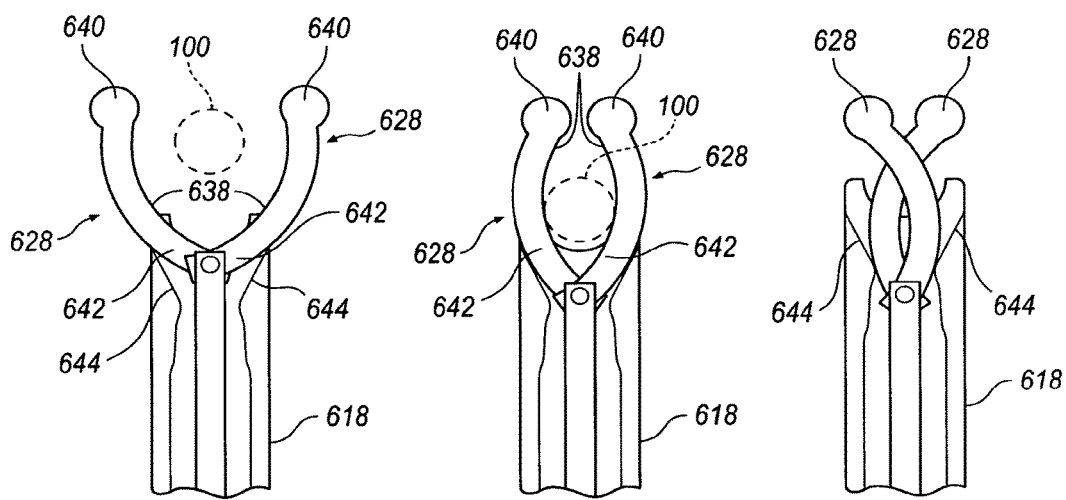
FIGS. 11A-11C illustrate enlarged perspective views of the distal end of the endocardial lead cutting apparatus of the sixth embodiment.

Referring to FIGS. 11A-11C, the blades 628 of the present embodiment are pivotally connected and may generally be described as have a scissor cutting action. The blades 628 are made of a generally hardened material such as hardened steel, carbide and the like. The blades 628 are general arcuate to define an inner cutting surface 638. Each blade 628 includes a first end 640 and a second end 642. The first ends 640 of the blades 628 are generally rounded or blunt-tipped to minimize damage to surrounding tissue when within a patient. The second ends 642 of the blades 628 are connected to the distal end 626 of the tension member 622.

The blades 628 are received within the housing 618 disposed at the distal end 616 of the tubular member 612. The housing 618 is preferably made from plastic and includes tapered sides 644. The tapered sides 644 urge the blades 628 to pivot about each other when moved from the extended position to the retracted position within the housing 618.

Optionally, the apparatus 10 of the sixth embodiment may also include a capture mechanism (not shown). The capture mechanism is disposed within the tubular member 612. The capture mechanism is preferably a wire, more preferably a deflectable guide or snare wire, made of a flexible or bendable material and having a biased arcuate distal end (also not shown). The capture mechanism is moveable between an extended position and a retracted position similar to the tension member 622 and the blades 628. When extended, the biased arcuate distal end wraps around the endocardial lead 100, by way of example only, by snaring the lead, to draw the lead 100 close to the distal end 616 and housing 618 of the tubular member 612. When retracted, the biased arcuate distal end is generally longitudinal and received within the housing 618 and tubular member 612.

In operation, the apparatus 10 of the sixth embodiment is placed within a patient. The capture mechanism is extended and the biased arcuate distal end wraps about the endocardial lead 100. The capture mechanism is retracted to draw the lead 100 close to the distal end 616 and housing 618 of the tubular member 612. The tension member 622 and blades 628 are extended as shown in FIG. 11A. The adjustment mechanism 620 is actuated and the tension member 622 and blades 628 are moved to the retracted position. As seen in FIG. 11B, the blades 628 pivot about each other at the second end 642 to capture the lead 100 between the inner cutting surfaces 638 of the blades 628. Further actuation and retraction of the tension member 622 and blades 628 cuts through the lead 100 as shown in FIG. 11C. The apparatus 10 is then removed from within the patient.

While the present invention has been particularly shown and described with reference to the foregoing preferred and alternative embodiments, it should be understood by those skilled in the art that various alternatives to the embodiments of the invention described herein may be employed in practicing the invention without departing from the spirit and scope of the invention as defined in the following claims. It is intended that the following claims define the scope of the invention and that the apparatus within the scope of these claims and their equivalents be covered thereby. This description of the invention should be understood to include all novel and non-obvious combinations of elements described herein, and claims may be present in this or a later application to any novel and non-obvious combination of these elements. The foregoing embodiments are illustrative, and no single feature or element is essential to all possible combination that may be claimed in this or a later application. Where the claims recite "a" or "a first" element of the equivalent thereof, such claims should be understood to include incorporation of one or more such elements, neither requiring nor excluding two or more such elements.

What is claimed is:

1. An endocardial lead cutting apparatus comprising:
   a flexible outer tubular member having a proximal end and a distal end;
   a flexible inner shaft having a proximal end and a distal end, said inner shaft received within said outer tubular member;
   a single blade extending from said distal end of said inner shaft;
   a first groove positioned at said distal end of said outer tubular member for receiving a lead; and
   a second groove positioned at said distal end of said outer tubular member for receiving the lead, wherein said outer tubular member has a distal arc length between said first groove and said second groove at said distal end;
   wherein said inner shaft rotates within said outer tubular member to cut the lead received in said positioning groove;
   wherein said single blade has a circular segment shape, said circular segment shape having an inner chord surface and an outer arc surface, wherein said outer arc surface has a blade arc length shorter than said distal arc length.

2. The apparatus of claim 1, wherein said first groove of said outer tubular member is generally V-shaped.

3. The apparatus of claim 1, wherein said single blade of said inner shaft is comprised of a hardened material.

4. The apparatus of claim 1, wherein the proximal end of said outer tubular member includes a handle.

5. The apparatus of claim 1, wherein the proximal end of the inner shaft includes a handle to rotate the inner shaft within the outer tubular member.

6. The apparatus of claim 1, wherein said second groove is positioned opposite of said first groove.

7. An endocardial lead cutting apparatus comprising:
- a flexible outer tubular member having a proximal end and a distal end;
- a flexible inner shaft having a proximal end and a distal end, said inner shaft received within said outer tubular member;
- a single blade extending from said distal end of said inner shaft;
- a first groove positioned at said distal end of said outer tubular member for receiving a lead; and
- a second groove positioned at said distal end of said outer tubular member for receiving the lead, wherein said outer tubular member has a distal arc length between said first groove and said second groove at said distal end;
- wherein said inner shaft rotates within said outer tubular member to cut the lead received in said positioning groove;
- wherein said single blade has a circular segment shape, said circular segment shape having an inner straight edge surface and an outer arc surface, wherein said outer arc surface has a blade arc length shorter than said distal arc length.

8. An endocardial lead cutting apparatus comprising:
- a flexible outer tubular member having a proximal end and a distal end;
- a flexible inner shaft having a proximal end and a distal end, said inner shaft received within said outer tubular member;
- a single blade extending from said distal end of said inner shaft;
- a first groove positioned at said distal end of said outer tubular member for receiving a lead; and
- a second groove positioned at said distal end of said outer tubular member for receiving the lead, wherein said outer tubular member has a distal arc length between said first groove and said second groove at said distal end;
- wherein said inner shaft rotates within said outer tubular member to cut the lead received in said positioning groove;
- wherein said single blade has a circular segment shape, said circular segment shape having an outer arc surface and an other surface, wherein said outer arc surface has a blade arc length shorter than said distal arc length, and wherein said outer arc surface comprises a first end point and a second end point, and wherein the other surface spans between the first end point and the second end point.

* * * * *